(12) United States Patent
Heidmann et al.

(10) Patent No.: US 9,212,369 B2
(45) Date of Patent: Dec. 15, 2015

(54) METHOD FOR PROVIDING FERTILE PLANTS VIA INDUCTION OF BBM DURING TRANSFORMATION

(75) Inventors: Iris Heidmann, Enkhuizen (NL); Kimberly Anne Boutilier, De Meern (NL); Brenda Johanna Maria De Lange, Venhuizen (NL)

(73) Assignees: Enza Zaden Beheer B.V., Enkhuizen (NL); Stichting Dienst Landbouwkundig Onderzoek, Wageningen (NL)

(*) Notice: Subject to any disclaimer, the term of this patent is extended or adjusted under 35 U.S.C. 154(b) by 867 days.

(21) Appl. No.: 13/383,312

(22) PCT Filed: Jul. 5, 2010

(86) PCT No.: PCT/EP2010/059540
§ 371 (c)(1),
(2), (4) Date: Mar. 29, 2012

(87) PCT Pub. No.: WO2011/003850
PCT Pub. Date: Jan. 13, 2011

(65) Prior Publication Data
US 2012/0192308 A1 Jul. 26, 2012

Related U.S. Application Data

(63) Continuation of application No. PCT/EP2009/058860, filed on Jul. 10, 2009.

(51) Int. Cl.
*C12N 15/82* (2006.01)
*C07K 14/415* (2006.01)
*A01H 4/00* (2006.01)

(52) U.S. Cl.
CPC ............ *C12N 15/8202* (2013.01); *A01H 4/008* (2013.01); *C07K 14/415* (2013.01); *C12N 15/8206* (2013.01); *C12N 15/8287* (2013.01)

(58) Field of Classification Search
None
See application file for complete search history.

(56) References Cited

U.S. PATENT DOCUMENTS

| 7,148,402 B2 * | 12/2006 | Niu et al. ................. 800/290 |
| 7,151,170 B1 * | 12/2006 | Boutilier et al. ............ 536/23.6 |
| 2007/0136895 A1 * | 6/2007 | Siddiqi et al. ............... 800/287 |
| 2008/0301836 A1 | 12/2008 | Century et al. |

FOREIGN PATENT DOCUMENTS

| EP | 1057891 A1 | 12/2000 |
| WO | 9746079 A1 | 12/1997 |
| WO | 2005075655 A2 | 8/2005 |
| WO | 2007092308 A2 | 8/2007 |
| WO | 2007135022 A1 | 11/2007 |

OTHER PUBLICATIONS

Irkova, T. et al. 2008. Dokladi NA Bolgarskata Akademiya Na Naukite, vol. 61, No. 6 pp. 761-770.*
Guo et al. (2004), Proc. Natl. Acad. Sci. USA 101: 9205-9210).*
Ouakfaoui, et al. Plant Mol Biol. (2010) 74:313-326.*
Ewart (Petunia Ch15. K.C. Sink ed. 1984, 180-202).*
Campbell (Master's thesis, Skye Campbell, Sep. 2008).*
Solis-Ramos et al. (Plant Cell Tiss Organ Cult (2009) 96:279-287).*
Irkova et al. (2008. Dokladi NA Bolgarskata Akademiya Na Naukite, vol. 61, No. 6 p. 761-770).*
Bent, Arabidopsis in Planta Transformation. Uses, Mechanisms, and Prospects for Transformation of Other Species, Plant Physiology, Dec. 2000, 1540-1547, vol. 124.
Boutilier et al., Ectopic Expression of Baby Boom Triggers a Conversion from Vegetative to Embryonic Growth, The Plant Cell, Aug. 2002, 1737-1749, vol. 14.
Broothaerts et al., Gene transfer to plants by a diverse species of bacteria, Nature, Feb. 10, 2005, 629-633, vol. 433.
Gamborg et al., Nutrient Requirements of Suspension Cultures of Soybean Root Cells, Experimental Cell Research, 1968, 151-158, vol. 50.
Irikova et al., Identification of Two Embryogenesis-related Genes in Sweet Pepper (*Capsicum annuum* L.) Genome, Compt. rend. Acad. bulg. Sci., 2008, 761-770,vol. 61, No. 6.
Maraschin et al., Androgenic switch: an example of plant emryogenesis from the male gametophyte perspective, Journal of Experimental Botony, Jul. 2005, 1711-1726, vol. 56, No. 417.
Murashige et al., A Revised Medium for Rapid Growth and Bio Assays with Tobacco Tissue Cultures, Physiologia Plantarum, 1962, 473-497, vol. 15.
Wang X et al., "Overexpression of PGA37/MYB118 and MYB115 promotes vegetative-to-embryonic transition in Arabidopsis", Cellular Research, vol. 2, p. 224-235 (Feb. 19, 2009).

* cited by examiner

*Primary Examiner* — Anne Kubelik
*Assistant Examiner* — Charles Logsdon
(74) *Attorney, Agent, or Firm* — The Webb Law Firm

(57) ABSTRACT

A method for providing a transgenic plant, including transforming a plant cell or plant material with a nucleotide sequence coding for a BBM protein, wherein activity of the BBM protein is induced during transformation and/or regeneration of the transformed plant cell or plant material, and wherein the plant cell or plant material originates from a recalcitrant plant is provided. In addition, a transgenic plant or material thereof having a BBM protein, wherein the transgenic plant is a recalcitrant plant is also provided.

15 Claims, 19 Drawing Sheets

SEQ ID No:1

MNNNWLGFSLSPYEQNHHRKDVYSSTTTTVVDVAGEYCYDPTAASDESSAIQTSFPSPFG
VVVDAFTRDNNSHSRDWDINGCACNNIHNDEQDGPKLENFLGRTTTIYNTNENVGDGSGS
GCYGGGDGGGGSLGLSMIKTWLRNQPVDNVDNQENGNAAKGLSLSMNSSTSCDNNNDSNN
NVVAQGKTIDDSVEATPKKTIESFGQRTSIYRGVTRHRWTGRYEAHLWDNSCKREGQTRK
GRQVYLGGYDKEEKAARAYDLAALKYWGTTTTTNFPMSEYEKEVEEMKHMTRQEYVASLR
RKSSGFSRGASIYRGVTRHHQHGRWQARIGRVAGNKDLYLGTFGTQEEAAEAYDIAAIKF
RGLTAVTNFDMNRYNVKAILESPSLPIGSAAKRLKEANRPVPSMMMISNNVSESENSASG
WQNAAVQHHQGVDLSLLHQHQERYNGYYYNGGNLSSESARACFKQEDDQHHFLSNTQSLM
TNIDHQSSVSDDSVFVCGNVVGYGGYQGFAAPVNCDAYAASEFDYNARNHYYFAQQQQTQ
QSPGGDFPAAMTNNVGSNMYYHGEGGGEVAPTFTVWNDN

Figure 16

SEQ ID No:2

```
TCTACAAAGAAAAAAATCAAAGGGATTCAGCAAGCCACTGCAGGAGTCTCACAAGACACT
TCGGAAAATCCTAACAAAACAATAGTTCCTGCTGCATTACCACAGCTCACCCCTACCTTG
GTGTCACTGCTGGAGGTGATTGAACCCGAGGTGTTGTATGCAGGATATGATAGCTCTGTT
CCAGATTCAGCGTGGAGAATTATGACCACACTCAACATGTTAGGTGGGCGTCAAGTGATT
GCAGCAGTGAAATGGGCAAAGGCGATACCAGGCTTCAGAAACTTACACCTGGATGACCAA
ATGACCCTGCTACAGTACTCATGGATGTTTCTCATGGCATTTGCCCTGGGTTGGAGATCA
TACAGACAATCAAGTGGAAACCTGCTCTGCTTTGCTCCTGATCTGATTATTAATGAGCAG
AGAATGTCTCTACCCTGCATGTATGACCAATGTAAACACATGCTGTTTGTCTCCTCTGAA
TTACAAAGATTGCAGGTATCCTATGAAGAGTATCTCTGTATGAAAACCTTACTGCTTCTC
TCCTCAGTTCCTAAGGAAGGTCTGAAGAGCCAAGAGTTATTTGATGAGATTCGAATGACT
TATATCAAAGAGCTAGGAAAAGCCATCGTCAAAAGGGAAGGGAACTCCAGTCAGAACTGG
CAACGGTTTTACCAACTGACAAAGCTTCTGGACTCCATGCATGAGGTGGTTGAGAATCTC
CTTACCTACTGCTTCCAGACATTTTTGGATAAGACCATGAGTATTGAGTTCCCAGAGATG
TTAGCTGAAATCATCACTAATCAGATACCAAAATATTCAAATGGAAATATCAAAAAGCTC
CTGTTTCATCAAAAATGACTG
```

Figure 17

SEQ ID No:3

```
atgaataataactggttaggcttttctctctctccttatgaacaaaatcaccatcgtaag
gacgtctactcttccaccaccacaaccgtcgtagatgtcgccggagagtactgttacgat
ccgaccgctgcctccgatgagtcttcagccatccaaacatcgtttccttctccctttggt
gtcgtcgtcgatgctttcaccagagacaacaatagtcactccgagattgggacatcaat
ggttgtgcatgcaataacatccacaacgatgagcaagatggaccaaagcttgagaatttc
cttggccgcaccaccacgatttacaacaccaacgaaaacgttggagatggaagtggaagt
ggctgttatggaggaggagacggtggtggtggctcactaggactttcgatgataaagaca
tggctgagaaatcaacccgtggataatgttgataatcaagaaaatggcaatgctgcaaaa
ggcctgtccctctcaatgaactcatctacttcttgtgataacaacaacgacagcaataac
aacgttgttgcccaagggaagactattgatgatagcgttgaagctacaccgaagaaaact
attgagagttttggacagaggacgtctataccgcggtgttacaaggcatcggtggaca
ggaagatatgaggcacatttatgggataatagttgtaaagagaaggccaaacgcgcaaa
ggaagacaagtttatttgggaggttatgacaaagaagaaaagcagctagggcttatgat
ttagccgcactcaagtattggggaaccaccactactaacttccccatgagcgaatat
gaaaagaggtagaagagatgaagcacatgacaaggcaagagtatgttgcctcactgcgc
aggaaaagtagtggtttctctcgtggtgcatcgatttatcgtggagtaacaagacatcac
caacatggaagatggcaagctaggataggaagagtcgccggtaacaaagacctctacttg
ggaactttggcacacaagaagaagctgcagaggcatacgacattgcggccatcaaattc
agaggattaaccgcagtgactaacttcgacatgaacagatacaacgttaaagcaatcctc
gaaagccctagtcttcctattggtagcgccgcaaaacgtctcaaggaggctaaccgtccg
gttccaagtatgatgatgatcagtaataacgtttcagagagtgagaatagtgctagcggt
tggcaaaacgctgcggttcagcatcatcagggagtagatttgagcttattgcaccaacat
caagagaggtacaatggttattattacaatggaggaaacttgtcttcggagagtgctagg
gcttgtttcaaacaagaggatgatcaacaccatttcttgagcaacacgcagagcctcatg
actaatatcgatcatcaaagttctgtttcggatgattcggttactgtttgtggaaatgtt
gttggttatggtggttatcaaggatttgcagccccggttaactgcgatgcctacgctgct
agtgagtttgattataacgcaagaaaccattattactttgctcagcagcagcagacccag
cagtcgccaggtggagattttcccgcggcaatgacgaataatgttggctctaatatgtat
taccatggggaaggtggtggagaagttgctccaacatttacagtttggaacgacaattag
```

Figure 18

METHOD FOR PROVIDING FERTILE PLANTS VIA INDUCTION OF BBM DURING TRANSFORMATION

FIELD OF THE INVENTION

The Sequence Listing associated with this application is filed in electronic format via EFS-Web and is hereby incorporated by reference into the specification in its entirety. The name of the text file containing the Sequence Listing is 114635_ST25.txt. The size of the text file is 9,058 bytes, and the text file was created on Jun. 28, 2013.

The present invention relates to a method for providing a mature transgenic plant, wherein the plant is a recalcitrant plant. The invention further relates to a mature transgenic plant, plant material, progeny, plant parts, seeds, or clones thereof, obtainable by the method of the invention. The invention also relates to the use of a mature transgenic plant or plant part thereof obtainable according to the method of the invention as a co-transformation system.

BACKGROUND OF THE INVENTION

Genetic transformation is a methodology used in the field of life sciences and as such used in various organisms for many purposes. This technology has had and has major implications in many areas of life sciences research. One aspect of the technology is that it can be used to identify functions of individual nucleotide molecules (e.g. genetic elements and/or genes) or proteins encoded by such nucleotide molecules. The resulting genetically modified organism can be used in fundamental or applied research or be used in an industrial application.

Genetic transformation can be a powerful technology in the field of plant sciences as it allows the transfer of a nucleotide molecule of interest to a receiving plant species. Such a nucleotide molecule can comprise promoters, genes, terminators, repressors or enhancers of gene of protein function, etcetera.

Genetic transformation can for example be used with the intention to study the effects of addition of a protein of interest to a receiving plant. In such cases, a gene that codes for the protein of interest, which is usually part of a larger nucleotide molecule, is introduced in the receiving plant.

In order to obtain a genetically modified plant, a method can be applied which comprises transformation followed by regeneration and subsequent development of transformed, regenerated plant material into a mature transgenic plant. Such a method can be successfully applied only to particular plant species that are responsive to both the transformation and regeneration phase and subsequent further development into a mature transgenic plant. Such plant species include for example *Arabidopsis thaliana* or *Brassica napes*.

During transformation a nucleotide molecule of interest is introduced into a plant cell. During regeneration, transformed plant material is allowed to develop from rather undefined structures, such as callus tissue, into plant organs, such as leaf like-structures, shoot-like structures or somatic embryos, such that a mature transgenic plant can be obtained therefrom.

The transformation phase can comprise contacting of a plant cell or plant material with an *Agrobacterium tumefaciens* bacterium which contains a Ti (Tumour-inducing) plasmid having the nucleotide molecule of interest. The Ti plasmid comprises at least a DNA segment which is transferred by *Agrobacterium tumefaciens* to a host-plant; the T-DNA element. The T-DNA element is flanked by DNA repeats, the so called left border and right border. Genetic engineering allows one to place a nucleotide molecule of interest between the left and right T-DNA border of the Ti plasmid. During contact of the plant cell or plant material with the *Agrobacterium tumefaciens* bacterium, at least the T-DNA element of the Ti plasmid, including the nucleotide molecule of interest, is transferred from the *Agrobacterium tumefaciens* bacterium into the plant cell where it is stably integrated in the nuclear genome or organellar genome, such as from a mitochondrion or chloroplast. Other methods of transformation may also be applied to plant material.

When considering suitable regeneration from a macroscopic point of view, regenerating plant cells or tissues may develop into an amorphous mass of cells (i.e. callus) from which a shoot-like structure or leaf-like structure can develop. Usually from such structures an elongated stem can develop, if needed under the influence of suitable plant hormones. Subsequently, such structures will, if needed under the influence of one or more suitable root-inducing agents, initiate formation of a root system to develop an advanced root system suitable to sustain further development. Subsequently, plant material of a suitable advanced stage of developmental can be transplanted from an in-vitro to an ex-vitro environment. The plant is subsequently grown ex-vitro, such as on soil, vermiculite, rock wool or the like, under suitable conditions which allow obtaining a mature transgenic plant. The regeneration procedure may comprise additional or alternative steps of this general concept. Alternatively, regeneration may proceed through the formation of somatic embryos which may be allowed to grow into mature plants.

Such a method of transformation and regeneration is preferably applied to young somatic plant tissues, cultured cells such as protoplasts or organs as starting material. Such tissues, such as explants of young plant tissue or pieces of plant material from seedlings, comprise cells of variable degrees of differentiation or determination. Likely due to the heterogeneous population of cells of various levels or degrees of differentiation which are present in such tissues, are such tissues in particular responsive to the initial phase of a regeneration treatment.

Only certain plants or plant species have been shown to be responsive to transformation and regeneration methods. It has been possible to apply existing methods to transform and regenerate such plants in a relatively straightforward manner. Conversely, it has become evident that other plants or plant species are unresponsive to such transformation and regeneration methods. Such plants do not regenerate in a suitable manner and/or cannot be made to regenerate at all into mature plants. Such plants, plant varieties or plant cultivars are called "recalcitrant" or "regeneration incompetent".

It is largely unknown which underlying molecular or physiological factors are responsible or that determine whether plants are recalcitrant or not. This indicates the current need for developing reliable plant-specific transformation and regeneration methods which can be applied to a wide variety of plant species. In fact, suitable transformation and regeneration methods for the efficient provision of mature transgenic plants have only been developed for a few species or cultivars of species.

A plethora of different problems has been observed and found to be insurmountable when recalcitrant plants were subjected to transformation and regeneration methods followed by development into mature transgenic plants. Such problems comprise inability to transform a plant cell from subjected plant cells or plant material. Or in case transformation can be achieved, such transformed material may not develop into a mature transformed plant. Transformed cells or plant material may regenerate up until a certain developmental stage, display aberrant behaviour such as altered or aberrant growth, premature termination of development, severely delayed development, or incorrect development. Also, the formation of false-positive plants is known to occur. Such non-transformed plant material may escape from the pressure of a selective agent and regenerate into a mature plant.

Furthermore, the following problems with respect to the applicability, reliability and suitability of the method are known: reproducibility can be problematic; the outcome of the method can be unpredictable, the amount of regenerating shoots, roots or plantlets may be too low for suitable application in an industrial setting; the method can only applied to a single plant species, or to a particular group of cultivars of a given plant species; the method may not be suitable for high-throughput or routine application; the method may depend on a specific bacterial strain for suitable applicability. It may be clear that such methods are not suitable for cost-efficient industrial applications. Hence, there remains a need for efficient and reliable methods for the provision of mature transgenic plants which can be applied to recalcitrant plant species.

SUMMARY OF THE INVENTION

Therefore, an object of the present invention is to provide a method for obtaining a mature transgenic plant, wherein the plant is a recalcitrant plant and wherein the method comprises a transformation phase and a regeneration phase. Furthermore, the object of the invention is to provide a transgenic plant, obtainable by the method of the invention.

The above object, amongst others, is provided by a method as defined in the appended claims.

Specifically, the present invention relates to a method for providing a mature transgenic plant, comprising transforming and regenerating a plant cell or plant material, wherein the plant cell or plant material is transformed with a nucleotide molecule comprising a nucleotide sequence coding for a babyboom (BBM) protein, wherein activity of the BBM protein is induced during transformation and/or regeneration of the transformed plant cell or plant material, and wherein the plant cell or plant material originates from a recalcitrant plant.

During the research that led to the invention it was found that plant material originating from several recalcitrant plants, such as sweet pepper and *petunia* W138, could be made to regenerate into mature transgenic plants by inducing BBM during transformation and regeneration, whereas without inducing BBM during these stages such plants did not develop into mature transgenic plants. Recalcitrant plants in the art and herein are plants which in essence do not regenerate and develop into a mature transgenic plant when plant material originating from such a plant is subjected to a for responsive plants suitable procedure of transformation and regeneration. The basis of such methods is that transformed plant material which is contacted with a medium comprising phytohormones, preferably auxin, cytokinin or gibberellic acids but also abscisic acid, ethylene or inhibitors thereof, allow regeneration of the transformed plant material as is the case for responsive plants. Herein a recalcitrant plant is a plant which cannot develop into a mature transgenic plant under any such conditions.

Quite a few recalcitrant plants, especially ones belonging to economically important plant species, crops or varieties, have been the subject of extensive research aimed at developing a suitable method for the provision of mature transgenic plants using regeneration. Considering that recalcitrant plants, such as sweet pepper, are notorious for their inability to regenerate into mature transgenic plants combined with the plethora of different problems that are encountered when attempting to transform and regenerate plant material from such plants into mature transgenic plants using prior art methods, is the efficiency of the present invention surprising.

An advantage of the present invention is that apparently a plant cell or plant material from a recalcitrant plant can, aided or not by the addition of one or more biologically active agents, such as a phytohormone or a substance that mimics an effect of a phytohormone, be made to develop into a mature transgenic plant. When used, such a biologically active agent can be added to the medium on which transformed plant material is cultured to allow the transgenic plant material to develop into a mature transgenic plant. Addition of such a biologically active agent to a plant cell or plant material in which activity of BBM was not induced did not allow such plant cell or plant material to regenerate into a mature transgenic plant.

Another advantage of the present invention includes the possibility to control the timing of BBM activity during the transformation and/or regeneration phases. Adjusting the temporal activity of BBM may allow further optimization of the quality or quantity of mature transgenic plants obtainable from recalcitrant plants through the present invention.

A further advantage of the present invention relates to the possibility to ensure suitable development of transformed plant material through reproductive developmental stages. By preventing inappropriate expression and/or activity of the BBM protein during reproductive stages of plant development, problems related to partial or complete sterility can be circumvented or alleviated.

Regeneration herein comprises the development of a transformed plant cell into a somatic embryo, a leaf-like structure or a shoot-like structure. In a subsequent phase such plant tissues can further develop into a mature transgenic plant.

The present invention thus allows for the first time to efficiently obtain mature transgenic plants from plant material originating from a recalcitrant plant by activating BBM during transformation and regeneration. With BBM activity herein is meant the effect of the expression of the transformed BBM on the transcription of genes of the transformed host plant. As BBM is a transcription factor, its activity comprises influencing the transcription of one or more BBM target genes. Activation of BBM can be accomplished by allowing BBM to become nuclear localized upon induction, but also by inducing its transcription or its translation. It is conceivable that activation of BBM causes induction or repression of transcription of its target genes by direct or indirect binding of BBM to a regulatory nucleotide and/or protein sequence. Irrespective of the underlying mechanism of BBM activity, the consequence of induced activity of a BBM protein expressed from an expression construct is that plant material originating from a recalcitrant plant which is subjected to transformation and regeneration can develop into a mature transgenic plants.

With "mature transgenic plant" herein is meant a plant which has reached an advanced stage of development such that the plant produces at least one reproductive organ, preferably more of such organs, such as a seed comprising fruit, wherein from such reproductive organ viable progeny can be obtained. The term "mature plant" herein is interchangeable with the term "fertile plant". Such a reproductive organ can be a sexual reproductive organ, such as a flower, or vegetative reproductive organ, such as a tuber, stolon, rhizome, corm, bulbil or a bulb. Of particular interest is a mature transgenic plant which can be obtained according to the present invention from which viable progeny can be obtained from a reproductive organ as described herein.

Herein a flower can be unisexual, i.e. having either at least a male reproductive organ (androecium) or at least a female reproductive organ (gynoecium); or herein a flower can be bisexual, i.e. having at least one male reproductive organ and at least one female reproductive organ.

A flower herein is preferably fertile, but can also contain either functional pollen of functional egg-cells. In case of a fertile flower, such a flower bears functional pollen and one or more functional egg cells, which can subsequently give rise to viable progeny. A flower with functional pollen and one or more functional egg-cells can produce one or more seeds by self-fertilization but also by cross-fertilization. In case of a flower containing either functional pollen of functional egg-cells, such a flower does not produce seed(s) from self-fertilization but can produce seed(s) from cross-fertilization. Such a flower can thus be male-sterile or female-sterile. A male sterile flower, however, can be fertilized by functional pollen from another flower. Pollen of a female-sterile flower can be used to fertilize another flower. The male sterility of such flower can be a result of cytoplasmic male sterility (CMS), sporophytic self-incompatibility, gametophytic self-incompatibility or any other sterility system. The above biological terms are used in their art-recognized meaning.

It is also conceived as a possibility to obtain an explant from primary transformed plant material from which a mature transgenic plant could be obtained. Such a mature transgenic plant obtained from an explant of a primary transformant also falls within the meaning of a mature transgenic plant according to the present invention and as a product directly obtained though the method of the present invention.

The term "plant cell" herein refers to any cell which is derived from a plant or plant material. Also meant is a protoplast or any cell from a liquid suspension or the like.

The term "plant material" herein refers to any explant, piece or cutting derived from any structure, tissue or organ from a plant. Plant material herein can also refer to any tissue or organ of a plant. Said plant tissue or organ from which said explant, piece or cutting is derived comprises a cotyledon, hypocotyl, epicotyl, seed, callus, leaf, root, shoot, flower, anther, pollen, ovule, egg cell, fruit, meristem, primordium, inflorescence, petiole, protoplast, sink tissue, source tissue, seedling, sink organ, source organ, tuber, zygotic embryo, somatic embryo or embryos deriving from doubled haploids of haploids. Also included in this respect are cell cultures such as single cell cultures, suspensions, androgenic culture, gynogenic cultures. In particular, the term plant material refers to seedling-derived tissue, such as a cotyledon or a piece thereof.

The term "transforming" herein refers to a method of introducing a nucleotide molecule, such as an expression vector or construct, into a receiving plant cell. Such a transformation procedure can be used to elucidate the function of a gene or protein or another genetic element, such as a promoter, enhancer, terminator or the like. The nucleotide molecule is preferably derived from a plant or based on a nucleotide sequence derived from a plant. The nucleotide molecule can also be of synthetic origin. The nucleotide molecule can be introduced in the plant cell by use of a bacterial vector such as *Agrobacterium tumefaciens* (see for example Bent, 2000) or another bacterium which is suitable for plant transformation (see for example Broothaerts et al., 2005). The transformation procedure can also comprise particle bombardment, mechanical injection or other transformation techniques that are suitable for use in the invention. Such technologies are all known by the skilled person and can be applied without performing inventive skill to practice the invention.

Another aspect of the present invention relates to the plant cell or plant material which is from a plant selected from the group consisting of the genera *Solanum, Petunia, Tulipa, Lilium, Crocus, Iris, Gladiolus, Spinacia, Beta, Chenopodium, Phaseolus, Pisum, Capsicum*, in particular a plant from the family of Solaneceae. The invention relates more in particular to the species *Solanum tuberosum, Petunia hybrida, Tulipa* spp, *Lilium* ssp, *Crocus*, ssp, *Iris* ssp, *Gladiolus* ssp, *Spinacea oleracea, Beta vulgaris, Chenopodium quinoa, Phaseolus vulgaris, Phaseolus coccineus, Pisum sativum* and *Capsicum annuum*, in particular a sweet pepper *Capsicum annum* plant. Several cultivars, varieties or types of these plant species and/or several plant species are notoriously recalcitrant and difficult to transform and/or regenerate into mature transgenic plants.

The invention relates in particular to recalcitrant potato (*Solanum tuberosum*) types or varieties, petunia (*Petunia hybrida*) types or varieties, such as W138, and more in particular to sweet pepper (*Capsicum annuum*) types or varieties, which, at least in case of sweet pepper, are considered and known by the skilled person to be notoriously recalcitrant.

The species *Capsicum annuum* has been divided into two groups based on the taste of the fruits, i.e. sweet (or mild) pepper types and hot (or chili) pepper types. The group of sweet pepper types comprises pepper plants bearing non-pungent, sweet tasting fruits. Such fruits have, at more advanced levels of maturity of the fruit, low levels of capsaicin (8-methyl-N-vanillyl-6-nonenamide) in the fruit. The sweet pepper group herein comprises blocky, bell, lamuyo, paprika, Hungarian paprika, New Mexican paprika, squash pepper, Spanish paprika, pimientio, Italian frying, Japanese Sweet, Viejo arruga dulce and Cuban varieties (De Witt & Bosland, 1997).

Sweet pepper is considered a highly recalcitrant *Capsicum annuum*. The following observations have been reported when sweet pepper plants were subjected to a method comprising transformation and regeneration: absence of formation of leaf primordia from calli; inability of leaf-like structures to proceed through the regeneration phase; absence of shoots in regenerating tissues; failure of shoot buds to elongate; development of shoot-like teratoma from shoot buds; failure of apical meristems to elongate; reduced apical dominance of regenerating shoots; regeneration of non-transgenic shoots from calli grown under selective pressure; reduced fertility of regenerating shoots, inability of a proper root system to develop from transgenic shoots or severely retarded growth of plant tissues or organs. Also the occurrence of false-positive plants, i.e. mature non-transgenic plants that do not contain a required resistance-conferring gene which enables plant growth under selective pressure, is known. It can thus be stated that the prior art does not teach a suitable, efficient or reliable method of transformation and regeneration for the provision of mature transgenic sweet pepper plants. The present invention has the advantage that a method to obtain mature transgenic sweet pepper plants is provided.

Application of the method according to the invention led to the provision of mature transgenic sweet pepper plants, in particular also to the provision of fully developed pepper fruits and viable seeds from these plants. Furthermore, the present invention can be used for the provision of germinating seedlings which comprise the exogenous BBM nucleotide sequence. Segregation analysis of self-fertilized mature transgenic plants demonstrated that the transgene was inherited by progeny of the next generation. Mendelian segregation of progeny of several mature transgenic plants corresponded to the presence of a single locus. Table 4 presents results from the segregation analysis. The present invention thus provided mature transgenic sweet pepper plants that produced viable progeny which comprised the transformed nucleotide sequence.

Transgenic sweet pepper seeds, obtained through the method of the present invention, were deposited under accession number NCIMB 41732. Seeds were deposited under the Budapest Treaty by Enza Zaden Research & Development located at Haling 1e, 1602 DB Enkhuizen in The Netherlands to NCIMB Ltd., an authorized International Depository Authority, located in the Ferguson Building on Craibstone Estate; Bucksburn, Aberdeen; AB21 9YA, Scotland. Seeds were deposited and tested for viability on Jul. 2, 2010 as *Capsicum annum* Fiesta —BBM and with the above-referenced accession number. The deposit was deemed viable and capable of reproduction as of Jul. 2 2010.

Another aspect of the invention relates to the BBM protein or a functional homolog thereof, which is characterized by having at least 50%, 60%, 70%, preferably 80%, more preferably 90%, even more preferably at least 95% identity and most preferably at least 98% identity to SEQ ID No 1 or wherein the BBM protein is SEQ ID No: 1. Whether a protein is a BBM homolog can be established by assessing whether the protein of interest causes similar expression of a reporter gene coupled to the promoter of a BBM target gene, than the BBM protein of SEQ ID No: 1. Such a target gene comprises, for example, Actin Depolymerizing Factor 9 (ADF9; GeneID:829649, TAIR:AT4G34970).

Alternatively, a candidate gene may be transformed into a sweet pepper plant using an expression vector encoding the candidate BBM protein which expression vector provides inducible nuclear transcriptional activity of said BBM candidate protein. Upon transformation into a plant cell from a sweet pepper plant, development of the subjected plant material into one or more mature transgenic plants will occur according to the invention. It lies well within the abilities of the skilled person to establish whether a gene or protein is a functional homolog of BBM according to the invention. In an initial exploration, the skilled person could consult contemporary electronic molecular biotechnological tools and databases provided by institutes such as the NCBI or any other such institute. Such tools and databases provide the skilled person with means to quickly assess if there would be any indication whether any unknown gene or protein could be a functional BBM homolog. Such indication could comprise information of an unknown sequence in relation to BBM with respect to evolutionary conservation and classification in related clades or the same Glade; whether the unknown sequence belongs to a BBM-related class of genes or proteins, such as the AP2 family which comprises ANT, PLT1, PLT2; sharing of a particular domain, such as the AP2 domain; the number of such shared domains, a single or repeated AP2 domain; nomenclature of genes or proteins, such as sequences termed BBM-like. Consequently, only a limited number of genes or proteins would in a second stage of investigation need to be transformed into a recalcitrant plant, in particular sweet pepper, to confirm whether the sequence of interest is a functional BBM-homolog. Following this procedure, the person skilled in the art of modern biotechnology would therefore be able to establish, without undue burden, whether a gene or protein could be a functional BBM homolog.

The term "sequence identity" herein is defined as the number of identical amino acids over the full length BBM protein according to SEQ ID No:1, divided by the number of amino acids of the full length and multiplied by 100. For example, a sequence with 90% identity with SEQ ID No:1 comprises over the full sequence of 579 amino acids of SEQ ID No:1, 521 identical amino acids, as exemplified by the following calculation: 521/579*100=90%.

BBM is conserved over a variety of different species, such as *Brassica napes, Arabidopsis thaliana, Medicago trunculata, Glycine max, Zea mays*. As disclosed in this application, is it possible to use a BBM gene from a plant from a taxon of the Crucifers (or Brassicaceae) to obtain, by a method comprising transformation and regeneration, a mature transgenic plant from the distinct and distant family of the Solanaceae. The level of evolutionary conservation likely renders these proteins suitable for application of the method over different recalcitrant plant species, spanning the Solaneceae, or even ranging from monocots to dicots.

TABLE 1

GI numbers (GenInfo identifier) of proteins of various plant species which resemble BBM of SEQ ID NO: 1.

| gi number | plant species |
| --- | --- |
| gi: 21069055 | *Brassica napus* |
| gi: 21069053 | *Brassica napus* |
| gi: 58761187 | *Medicago trunculata* |
| gi: 21069057 | *Arabidopsis thaliana* Col 0 |
| gi: 151936654 | *Arabidopsis thaliana* C 24 |
| gi: 46451393 | *Arabidopsis thaliana* |
| gi: 9755766 | *Arabidopsis thaliana* |
| gi: 195615496 | *Zea mays* |
| gi: 195612040 | *Zea mays* |
| gi: 21304227 | *Oryza sativa* |
| gi: 189170271 | *Pennisetum squamulatum* |
| gi: 189170265 | *Pennisetum squamulatum* |
| gi: 189170267 | *Cenchrus ciliaris* |
| gi: 189170269 | *Cenchrus ciliaris* |

Yet another aspect of the invention relates to the nucleotide sequence coding for a BBM protein which is operably linked to a genetic element selected from the group consisting of a transcriptional activator, a translational activator or a nuclear targeting system.

Such genetic elements allow control of the activity of the BBM protein to enable suitable spatial and/or temporal activity of the BBM protein. Spatial activity herein means that organ or tissue specific BBM activity can be achieved. An advantage of using such genetic elements is that the occurrence of problems related to inappropriate expression or activity of the BBM protein can be prevented.

In a preferred embodiment is the BBM protein operably linked a nuclear targeting system. In this embodiment it is possible to control the activity of BBM by causing the BBM::GR translationally fused protein to migrate or translocate to the nucleus.

When the genetic element according to the invention is a transcriptional activator, it is possible to regulate the activity of BBM on a transcriptional level. Such a transcriptional induction system can be a system which comprises an ethanol inducible promoter or a heat-shock inducible promoter. A translational activator, which could be placed in the 5'UTR or 3'UTR sequence, can be used to regulate BBM activity by translational control. It will be clear to the skilled person which systems can be used to induce BBM activity according to the above mentioned genetic elements. Other suitable systems include an oestrogen inducible system, a PRP inducible system, a UAS inducible system, any VP16 comprising system.

In a preferred embodiment of the present invention is the nucleotide sequence coding for a BBM protein operably linked to a nucleotide sequence characterized by SEQ ID No: 2. The peptide encoded by this nucleotide sequence allows activity of the BBM protein to be induced when plant material is contacted with a medium comprising dexamethasone (DEX).

In another preferred embodiment of the present invention the regenerating transformed plant cell or plant material is contacted with a medium comprising an agent suitable for induction of activity of the BBM protein.

In yet another embodiment of the invention is ethanol the agent which is suitable for induction of activity of the BBM protein. In this embodiment, ethanol may be used to induce transcription of the exogenous BBM gene. Other systems for induction of transcription are also suitable to practice the invention. The activity of BBM could also be regulated on other levels, such as translational or post-translational level, to practice the invention.

According to an embodiment of this aspect, the expression vector further encodes one or more selectable markers, one or more proteins of interest and/or one or more transcription products of interest. Such proteins of interest comprise any protein providing resistance to any pathogen of interest, but also a protein which is part of a pathway leading to the production vitamins, nutrients, sugars, and the like.

The invention further relates to a mature transgenic plant or material thereof, obtainable by a method as described above, comprising a exogenous nucleotide sequence comprising a nucleotide sequence coding for a BBM protein and a genetic element suitable for allowing induction of activity of the BBM protein, wherein the mature transgenic plant is a recalcitrant plant. In a preferred embodiment of the invention, the mature transgenic plant is a plant selected from the group consisting of a recalcitrant plant from the genera *Solanum, Petunia, Tulipa, Lilium, Crocus, Iris, Gladiolus, Spinacia, Beta, Chenopodium, Phaseolus, Pisum* and *Capsicum*, in particular a plant from the Solaneceae.

In a more preferred embodiment of the invention is the mature transgenic plant a sweet pepper *Capsicum annuum* plant.

The mature transgenic plant according to the invention comprises a exogenous BBM protein, or functional homolog which is characterized by having at least 50%, 60%, 70% identity, preferably at least 80% identity, more preferably at least 90% identity, even more preferably at least 95% identity and most preferably at least 98% identity to SEQ ID No 1 or wherein the exogenous BBM protein is SEQ ID No: 1. Preferably, the mature transgenic plant comprises in its genome a exogenous nucleotide sequence which codes for the BBM protein according to the invention.

Herein, an exogenous nucleotide sequence is a nucleotide sequence which has been introduced in plant material through a biotechnological procedure, such as transformation. An exogenous protein is a protein which is encoded from the exogenous nucleotide sequence.

In yet another embodiment of the invention is the genetic element suitable for allowing induction of activity of the exogenous BBM protein selected from the group consisting of a transcriptional activator, translational activator or preferably a nuclear targeting system.

An advantage of the invention is that activity of the exogenous BBM protein can be induced, in both a spatial and temporal manner, to allow suitable activity or expression of the BBM protein. It appears especially advantageous that, besides the possibility to induce exogenous BBM activity during transformation and/or regeneration, exogenous BBM activity can be reduced or be absent during developmental stages wherein exogenous BBM activity could have unfavourable, adverse effects. Spatial activity of exogenous BBM could be controlled using tissue-specific promoters. For example, use of a promoter which is not active during reproductive stages of plant development could prevent sterility-related problems. Use of a promoter which is active during stages of seedling growth and development could be preferred during regeneration of transformed plant material.

Genetic elements according to the invention are operably linked to the exogenous BBM gene to allow suitable activity of exogenous BBM. Suitable elements comprise any heat-shock inducible system, ethanol inducible system, oestrogen inducible system, PRP inducible system, UAS inducible system, any VP16 comprising system. For the skilled person it is clear which other suitable systems could be used to practice the invention and which biotechnological methods to use to produce such a system.

It is furthermore conceived possible to control BBM activity according to the present invention by methods based on the use of a dominant repressor, a dominant activator, an anti-sense construct, an RNAi construct, siRNA construct, a knock-out, or other such methods that sort the same effect of influencing BBM activity.

A preferred embodiment of the invention relates to the genetic element suitable for allowing induction of activity of the BBM protein which is characterized by SEQ ID No 2. This genetic element can be operably linked, which results in a translational fusion, to the BBM protein. Such an operable linkage allows the BBM protein to become localised in the nucleus of a transgenic cell through which induction of BBM activity is allowed. In this embodiment, activation of exogenous BBM is mediated by the peptide encoded by SEQ ID No:2 which allows activity of the BBM protein to be induced when plant material is contacted with a medium comprising dexamethasone.

Furthermore, the invention relates to progeny, plant parts, seeds or clones of a mature transgenic plant according to the invention. An advantage of the invention is that progeny can be obtained from a mature transgenic plant according to the invention. Such progeny can be obtained from a mature transgenic plant for example by a-sexual propagation from tissues or organs. In such a case, progeny can be obtained by suitable methods for propagating a cell, tissue, organ or any suitable plant part. Such method may comprise cloning of plant material by various means, grafting, propagation of leaf cuttings, rooting of cuttings, or other such suitable methods. Propagation methods can also comprise technologies based on preparation of gametes to obtain progeny. Such technologies comprise production of doubled-haploid progeny by gynogenesis or androgenesis. Also envisioned for obtaining progeny are suitable methods comprising plant tissue culture or plant cell culture.

It is also considered possible to practice the invention by cloning a BBM gene according to the invention into a genetic construct which comprises nucleotide sequences that allow a BBM coding nucleotide sequence to be excised, recombined or lost from the genome of a plant cell. Such a system includes for example the Cre-Lox system or the FLP/FRT system, but may also comprise another suitable recombination system.

It is further noted that transgenic and/or non-transgenic progeny may be obtained from a mature transgenic plant according to the present invention. Such progeny can be obtained by cross-fertilizing or self-fertilizing the mature plant allowing segregation of the transgene according to Mendelian laws. Non-transgenic progeny may be obtained by self-fertilization of a mature transgenic plant which is heterozygous for the transgene or by crossing a mature transgenic plant with any other suitable plant which does not comprise a BBM transgene via which non-transgenic progeny can be obtained.

Another aspect of the invention relates to the use of a mature transgenic plant or plant part obtainable according to the method of the present invention as a co-transformation system. The scope of the present invention herein also encompasses the use of a nucleotide molecule which comprises an inducible BBM nucleotide sequence according to the invention as a basis for a co-transformation system, preferably as a marker-free system.

Herein several embodiments are envisioned; in a first embodiment is plant material from a exogenous inducible BBM-comprising plant, such as a T1 or higher sweet pepper plant, transformed with another expression construct which may comprise a gene of interest. This T1 or higher plant may be heterozygous or homozygous for the exogenous inducible BBM transgene. In a second embodiment is plant material originating from a non-transgenic recalcitrant plant transformed (and regenerated to a mature transgenic plant) with an expression construct which comprises, besides a nucleotide sequence coding for an inducible BBM protein, another nucleotide sequence which can code for one or more genes of interest or one or more genetic elements of interest. An advantage of this strategy is that the inclusion of a nucleotide sequence coding for an inducible BBM protein allows efficient marker-free transformation and regeneration as in essence each obtained mature plant will comprise the inducible BBM construct and the further nucleotide sequence of interest.

In a further embodiment, a non-transgenic recalcitrant plant cell or material is transformed with an expression construct which comprises a nucleotide sequence coding for an inducible BBM protein and a second, different, expression construct which comprises a further nucleotide sequence of interest. Preferably, recalcitrant plant cell or plant material is simultaneously contacted with both expression constructs. This further nucleotide sequence of interest may or preferably codes for a further protein of interest. An advantage of these embodiments is that recalcitrant plant species, e.g. sweet pepper, can be transformed and regenerated with essentially any nucleotide sequence or gene of interest. Such nucleotide sequence of interest can be selected from an RNAi sequence or antisense sequence directed at a sequence of interest, an overexpression sequence, gain-of-function sequence, or any other sequence of interest.

Both embodiments allow obtaining a mature transgenic plant, such as sweet pepper, which comprises, besides exogenous BBM, any other nucleotide molecule of interest.

The first embodiment related to the co-transformation system has a further advantage in the sense that a exogenous BBM comprising transgenic plant can first be selected based on a suitable phenotype or genotype. A suitable phenotype may include a sufficiently growing or developing plant or a plant having suitable fertility or any other suitable or preferred phenotype. A suitable genotype may relate to the stability of the transgene, the level of expression of BBM such as caused by a position effect, the leakiness of the construct, i.e. inappropriate activity of BBM, the number of transgenes in a single plant, the number of constructs present at a single integration site in a single plant (multiple copies of the T-DNA construct may be inserted at a single locus) or any other suitable or preferred property.

The second embodiment related to the co-transformation system has a further advantage in the sense that it allows to obtain a recalcitrant plant comprising, besides exogenous BBM, any other nucleotide sequence of interest, in a single transformation and regeneration treatment.

It is especially noted here that it is possible to use protoplasts for such co-infection or co-transformation in both these embodiments.

Thus, additionally or alternatively, a method for obtaining a mature transgenic plant is provided, comprising inducing BBM activity in a transformed plant cell or in transformed plant material during regeneration thereof, wherein the plant cell or plant material comprises a exogenous nucleotide molecule comprising a nucleotide sequence coding for a BBM protein which is operably linked to a genetic element suitable for allowing induction of activity of the BBM protein, and wherein the plant cell of plant material is derived from a recalcitrant plant, in particular sweet pepper. When desired, the transgenic plant cell or transgenic plant material is regenerated into a mature transgenic plant. The plant cell or plant material can be derived from a T1 or higher transformant. This plant is preferably homozygous but can also be heterozygous for the inducible-BBM transgene.

Regeneration can be achieved by contacting the transformed plant cell or plant material with a medium comprising an agent suitable for induction of activity of the BBM protein.

As the T1 or higher plant comprises a BBM protein of which its activity can be induced, the respective recalcitrant plant is rendered regeneration-competent upon BBM activation. This opens the possibility that the transformed plant cell or plant material can be transformed with another nucleotide molecule comprising a further nucleotide sequence of interest, in particular a nucleotide sequence coding for a protein of interest, and to regenerate this plant material into a mature transgenic plant. This second nucleotide sequence of interest may also comprise an RNAi sequence or antisense sequence directed at a sequence of interest, an overexpression sequence, gain-of-function sequence, or any other sequence of interest. Having a regeneration competent recalcitrant plant, due to the presence of a exogenous BBM protein which activity can be induced, is in particular of interest for sweet pepper which can now for the first time be efficiently transformed and regenerated to maturity, in essence with any nucleotide sequence or gene of interest. In this embodiment, the method is thus used as a co-transformation system as meant herein.

Alternatively, the regeneration of plant cells or plant material which comprise a nucleotide sequence coding for an inducible BBM protein can be used for plant-multiplication purposes as transgenic plants comprising a nucleotide sequence coding for an inducible exogenous BBM protein develop numerous somatic embryos when contacted with a cultivation medium comprising an agent suitable for induction of BBM as meant herein. Preferably, this medium also comprises a suitable amount of a cytokinin, such as thidiazuron, zeatin or 6-benzylaminopurine, when even more somatic embryos are desired. As the number of clearly distinguishable somatic embryos on the surface of cotyledon explants was found to exceed at least 100, it is possible to isolate these embryos and allow them to germinate and develop further into mature transgenic plants. This plant material which can be multiplied is preferably derived from explants, in particular cotyledon explants.

Additionally, material or cells from growing or maturing plant material derived from somatic embryos may be subjected to another round of multiplication by inducing BBM during regeneration resulting in the provision of somatic embryos therefrom.

A final aspect of the invention relates to the use of a nucleotide molecule for transformation and regeneration of plant material into a mature transgenic plant, wherein the plant material originates from a recalcitrant plant, wherein the nucleotide molecule comprises a nucleotide sequence coding for a BBM protein, wherein the BBM protein is characterized by having at least 50%, 60%, 70%, preferably at least 80%, more preferably at least 90%, even more preferably at least 95% and most preferably at least 98% identity to SEQ ID No 1 or wherein the BBM protein is characterized by SEQ ID No: 1.

In a preferred embodiment of this aspect of the invention is the nucleotide sequence coding for a BBM protein operably linked to a genetic element suitable for allowing induction of activity of the BBM protein.

In another preferred embodiment of this aspect of the invention is the genetic element suitable for allowing induction of activity of the BBM protein selected from the group consisting of a transcriptional activator, translational activator or preferably a nuclear targeting system.

In yet another preferred embodiment of this aspect of the invention is the genetic element suitable for allowing induction of activity of the BBM protein SEQ ID No:2.

In a final preferred embodiment of this aspect of the invention is the recalcitrant plant selected from the group consisting of the genera *Solanum, Petunia, Tulipa, Lilium, Crocus, Iris, Gladiolus, Spinacia, Beta, Chenopodium, Phaseolus, Pisum* and *Capsicum*, in particular a plant from the family of Solanaceae, more in particular a sweet pepper *Capsicum annuum* plant.

DETAILED DESCRIPTION OF THE DRAWINGS

In this application reference is made to the following figures:

FIG. 1 shows a phylogenetic tree of BBM proteins from various plant species.

FIG. 2 demonstrates a 3 week old explant with callus formation

FIG. 3 demonstrates callus and SLS formation of the control.

FIG. 4 demonstrates somatic embryo formation on SLS on explants transformed with 35S::BBM:GR.

FIG. 5 demonstrates elongating shoots

FIG. 6 demonstrates a rooted shoot

FIG. 7 demonstrates a transgenic red blocky type

FIG. 8 demonstrates a transgenic yellow blocky type

Figure 13:
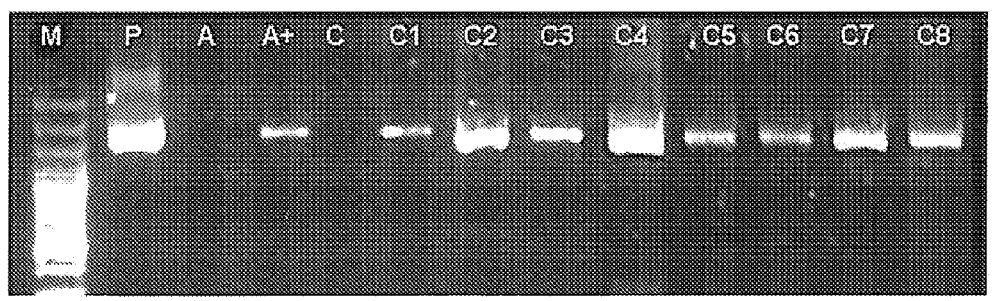

FIG. 13 displays a gel of a PCR result performed on transgenic pepper plants. Lane: M, molecular marker; P, 35S:: BBM:GR plasmid DNA; A, non-transgenic *Arabidopsis*; A+, transgenic *Arabidopsis*; C, non-transgenic pepper; C1-4 independent transgenic sweet peppers; C5-8 transgenic pepper shoots deriving from the same explant.

Figure 14:
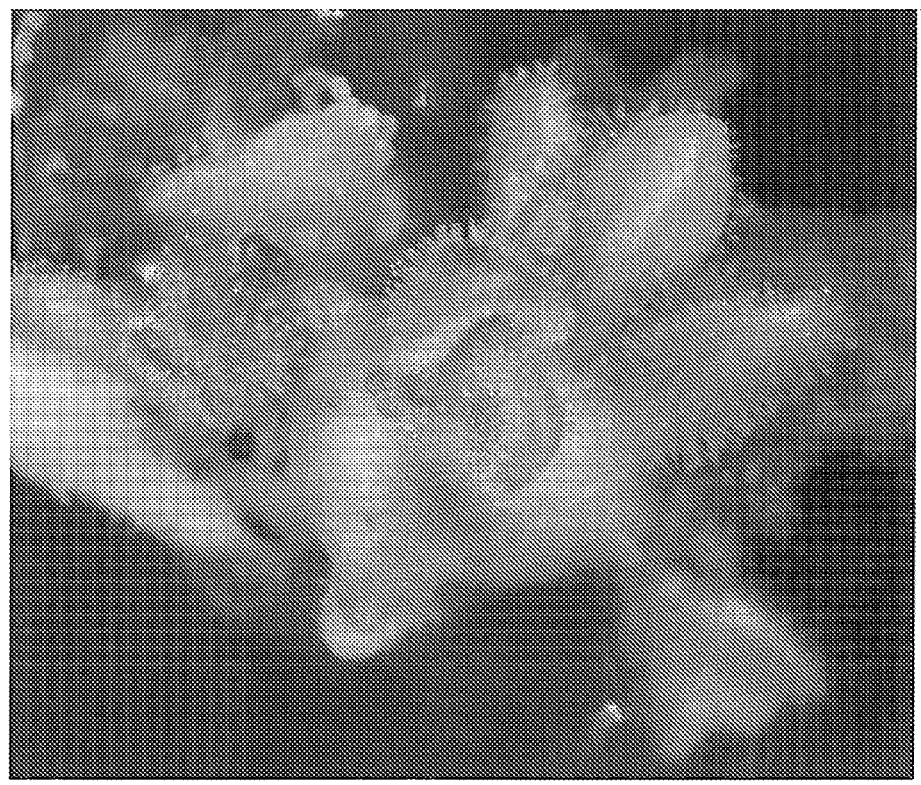

FIG. 14 demonstrates shoot regeneration of transgenic *petunia* of W138 background.

Figure 15:
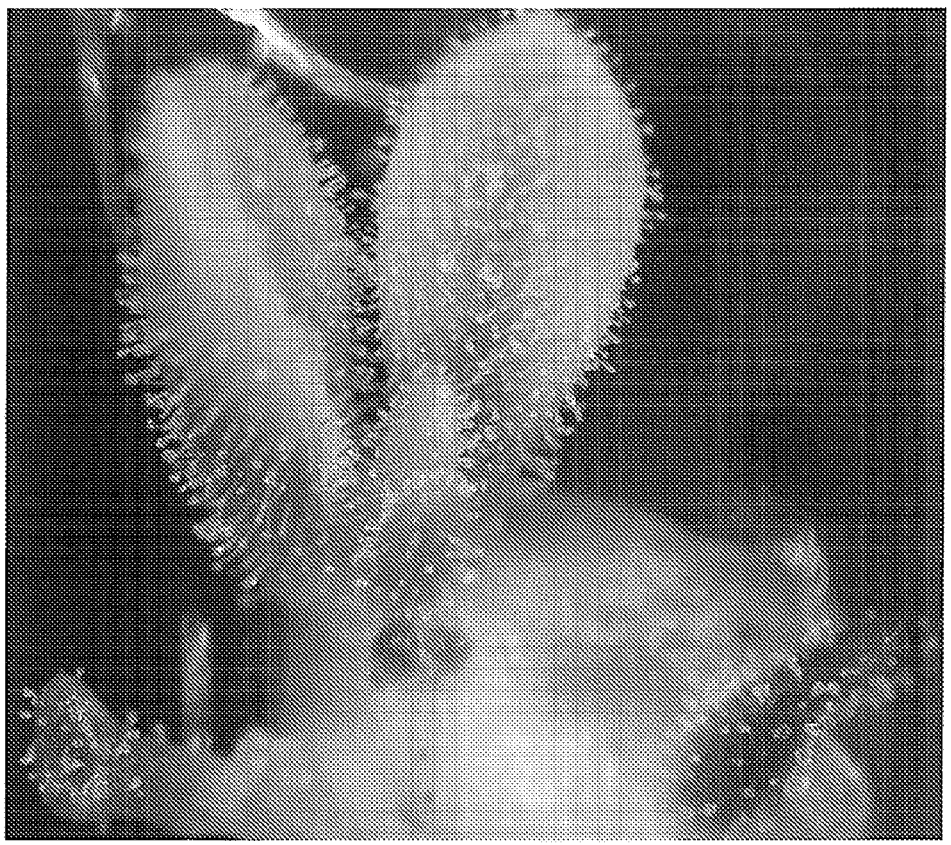

FIG. 15 demonstrates shoot regeneration of transgenic *petunia* of W138 background.

FIG. 16 shows SEQ ID No:1.

FIG. 17 shows SEQ ID No:2.

FIG. 18 shows SEQ ID No:3.

Figure 19:
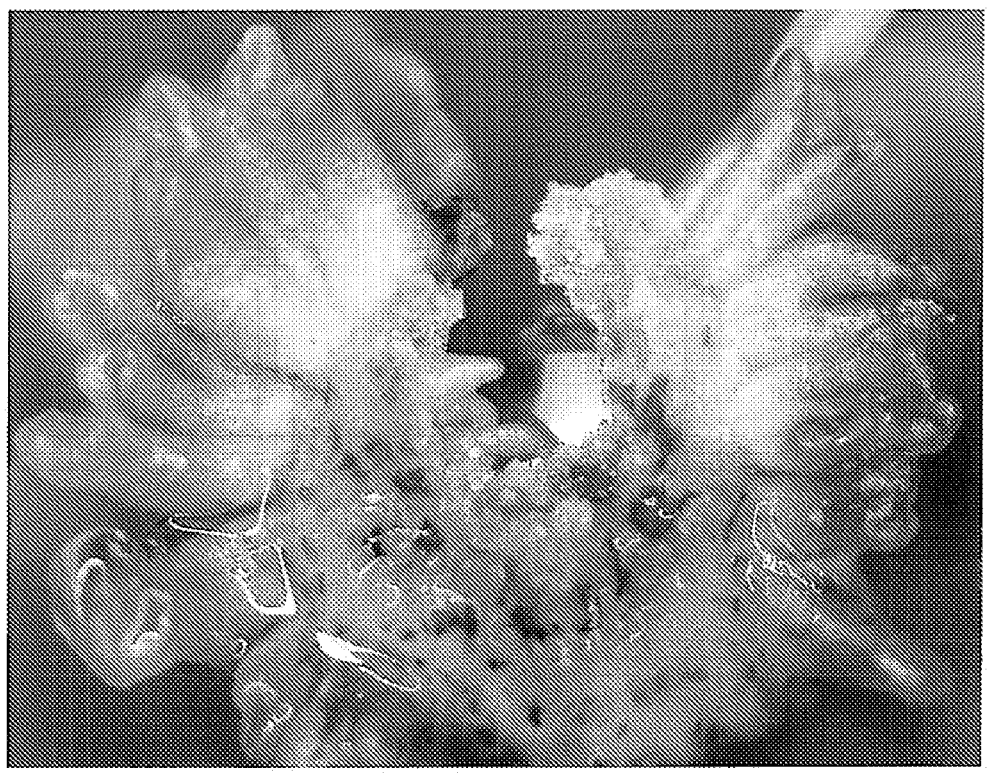

FIG. 19 demonstrates somatic embryo formation at the rim of a wound-site in T1 progeny of a 35S::BBM::GR comprising sweet pepper transgenic line, after induction of nuclear transcriptional babyboom activity.

The present invention is further illustrated by the following examples that are not intended to limit the scope of the invention in any way.

EXAMPLES

Example 1

Genetic Transformation of Sweet Pepper with BBM

Genetic transformation of sweet pepper plants of the species *Capsicum annuum* comprising SEQ ID No: 1 and SEQ ID No: 2. Plants from the phenotypically and genotypically distinct varieties Fiesta, Ferrari and Spirit were used.

Growth of Donor Plants

Surface sterilized seeds of F1 hybrids Fiesta, Ferrari and Spirit (Enza Zaden, The Netherlands) were sown on full strength MS medium (Murashige and Skoog, 1962) supplemented with 2% sucrose, solidified with 0.8% Microagar (Duchefa). Ten day old cotyledons were cut into explants of 3-10 mm and pre-cultured on co-cultivation medium (CCM) for 1-2 day under dim light conditions at 23° C. CCM comprises modified R medium supplemented with 1.6% glucose and 2 mg/l zeatin riboside, 0.1 mg/l Indole-3-acetic acid (IAA), or 0.25-1 mg/l Thidiazuron (TDZ), 10 µM Dexamethasone and solidified with 0.7% Microagar. An average of 200 explants was used per construct in 6-10 independently repeated experiments.

Growth of *Agrobacterium tumefaciens*

*Agrobacterium tumefaciens* strain GV3101+pMP90 carrying the 35S::BBM:GR (comprising the 35S promoter which is operably linked to the BBM coding sequence (SEQ ID No:1) to which the Glucocorticoid Receptor (GR) is translationally fused (SEQ ID No:2)), 35S::BBM (comprising the 35S promoter, operably linked to the BBM coding sequence SEQ ID No.1) or a control plasmid carrying 35S::GUS were grown in the presence of appropriate antibiotics, Rifampicin (100 mg/l), Kanamycin sulfate (100 mg/l), and/or Gentamycin (25 mg/l) in 100 ml YEB medium (0.5% yeast extract, 0.5% beef extract, 2% sucrose, pH7.2) as an overnight culture at 28° C. Prior to plant transformation, *Agrobacterium tumefaciens* suspension was diluted to OD660 0.3-0.4 with liquid CCM supplemented with 40 mg/l freshly prepared acetosyringone (Sigma).

Genetic Transformation of Plant Material

The diluted *Agrobacterium tumefaciens* culture was added to the pre-cultured explants and incubated at room temperature for 30-60 minutes. Explants were blotted dry and further co-cultured on CCM supplemented with 40 mg/l Acetosyringone for 2-3 days under dim light conditions at 23° C. before transferred to selective medium consisting of the CCM supplemented with 100mg/l Kanamycin sulfate and 500 mg/l Cefotaxime.

Regeneration of Transgenic Plant Material

Explants were transferred to full light conditions under a 16/8 h day/night regime at 23° C. for two months with one sub-culture after four weeks. Explants with emerging shoot-like structures were transferred for a period of four weeks to elongation medium (EM) consisting of macro- and micro-salt mixture of MS medium (Murashige and Skoog 1962), vitamins according B5 medium (Gamborg O. L. 1968), 1.6% glucose, 1 mg/l inositol, 20 mg/l Adenine sulfate, 200 mg/l Casein hydrolysate, 10 mg/l GA3, 4 mg/l BAP, 30 µM Silverthiosufate, 100 mg/l Kanamycine sulfate, and 500 mg/l Cefotaxime. Elongated shoot were transferred for a period of two months to pre-rooting medium (PRM), modified MS medium supplemented with 30 mg/l glutathione, 60 ml/l kanamycin sulfate, and 300 mg/l Cefotaxime and then to rooting medium, consisting of Rugini medium supplemented with 2% sucrose, 50 mg/l Cefotaxime and Vancomycine, with or without 1 mg/l IAA. Rooted shoots were transferred to the greenhouse to allow seed set to occur. All tissue culture related chemicals were supplied by Duchefa Biochemicals, Haarlem, The Netherlands.

Analysis of Transgenic Shoots

DNA was isolated form leaves via a CTAB mini-preparation method and dissolved in 50 µL TE (10 mM Tris pH 8, 1 mM EDTA). BBM specific primers were designed based on the published cDNA sequences (AF317904, and −905), BBMfw: gttaggyttytctctmtctcc,BBMrw: gggctgcaaatcct-tgataacca. DNA from the transformed plasmid and a transgenic Arabidopsis lines were used as controls. PCR mixture was used according the protocol of the supplier. PCR conditions: 15 sec 94° C.; 30 sec 48° C.: 45 sec 72° C.; 35 cycles. Results are presented in FIG. 13.

Analysis of Transgenic Offspring

Each individual transgenic shoot was self-pollinated and also crossed with a plant from the original donor line to analyze inheritance of the transgene. After harvesting seeds were surface sterilized and sown onto MS medium, 2% sucrose, 0.8% microagar, and 200 mg/l Kanamycin sulphate or 100 ml/L Paromomycin sulfate. Segregation was evaluated 4 weeks after sowing.

Results

Figure 1:
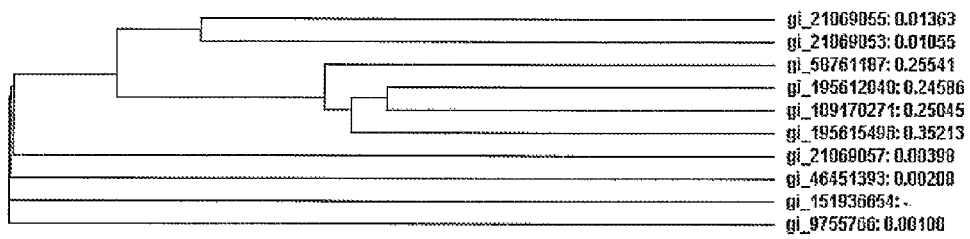
Figure 2:
Figure 3:
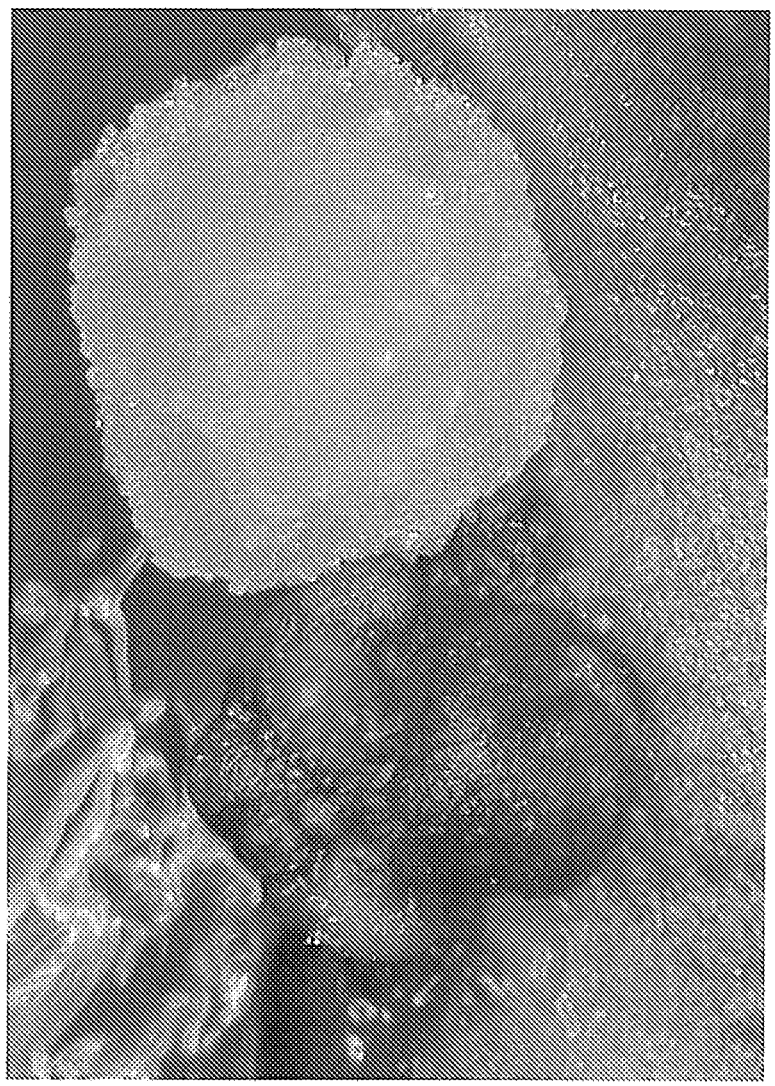
Figure 4:
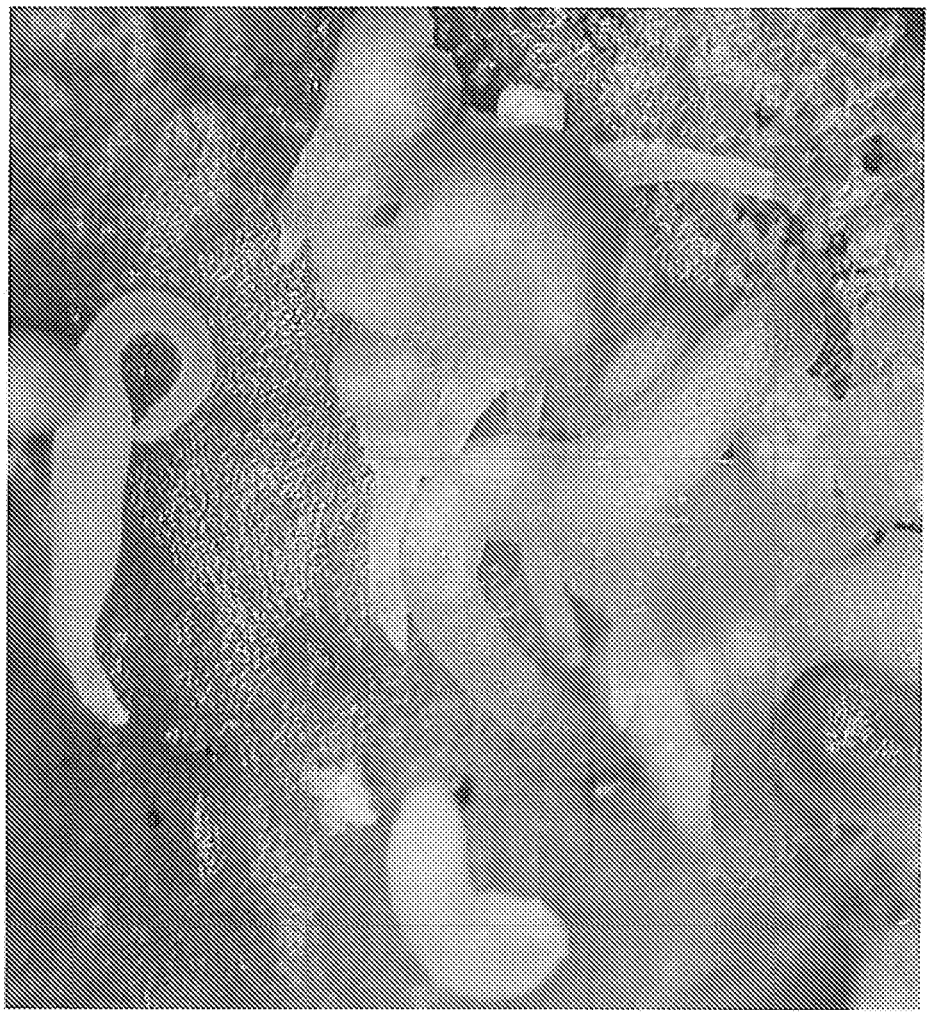
Figure 5:
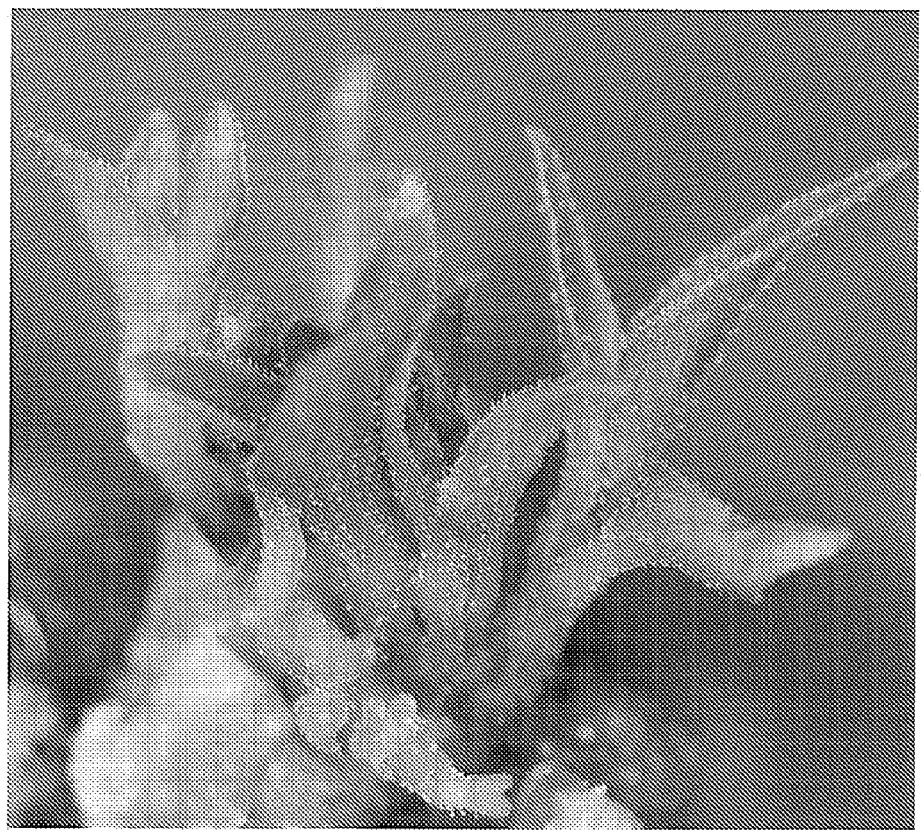
Figure 6:
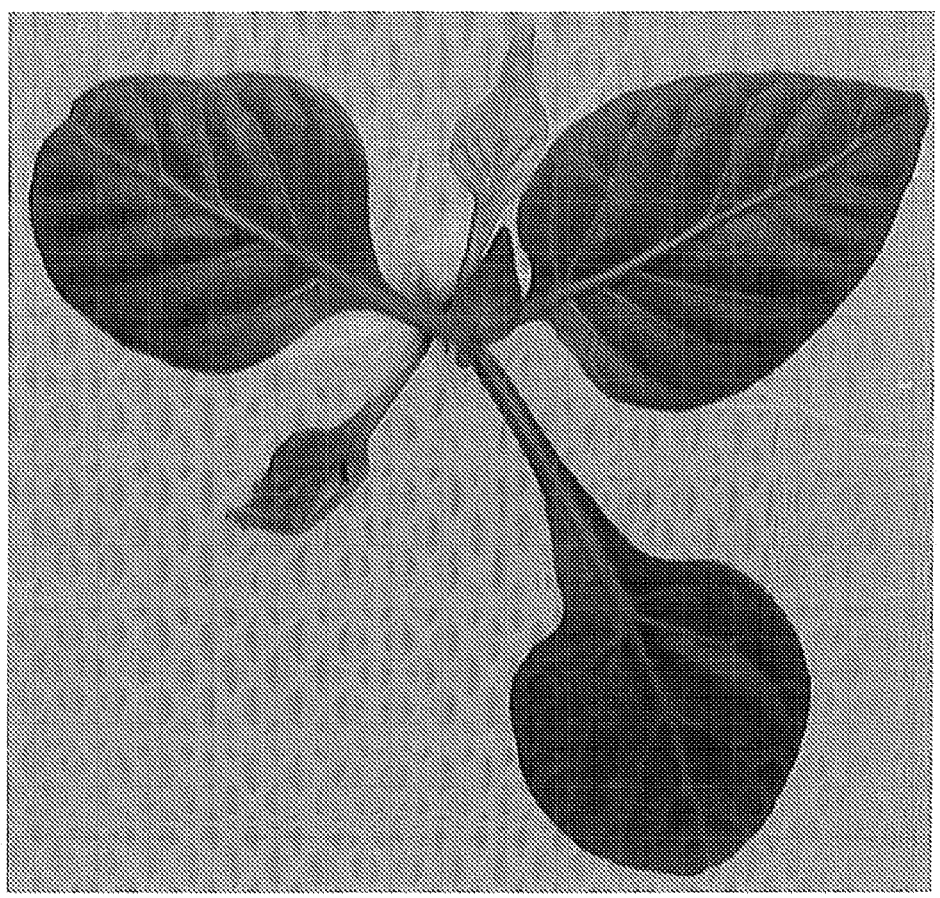
Figure 7:
Figure 8:
Figure 9:
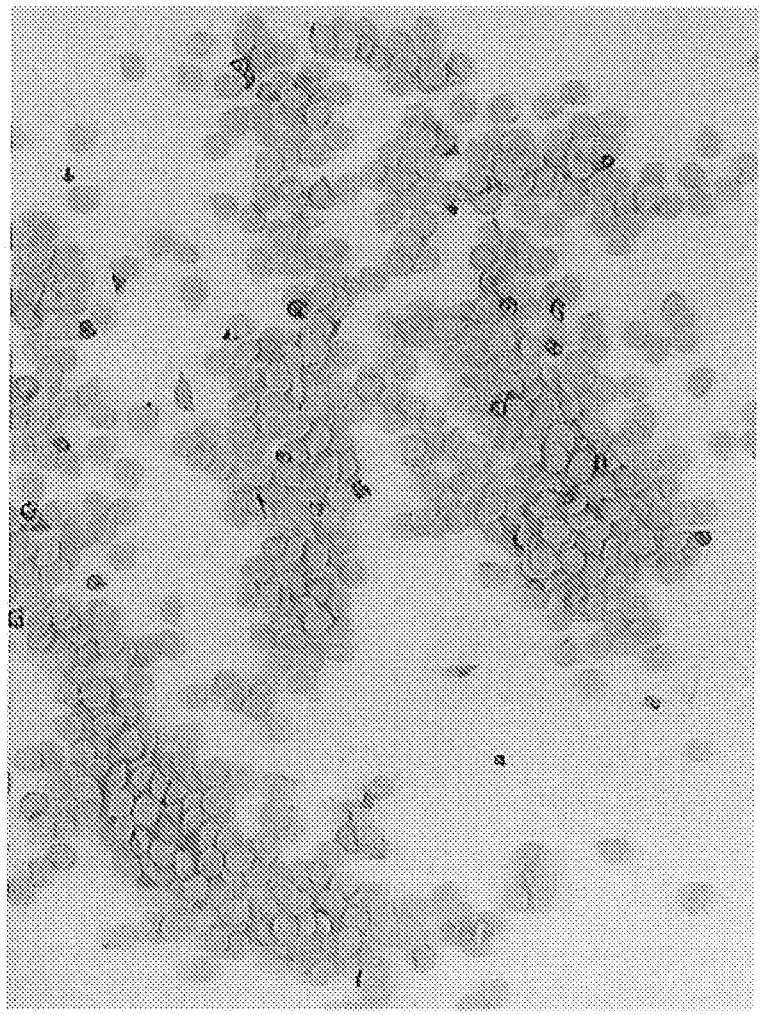
FIG. 9 shows seeds of transgenic plants
Figure 10:
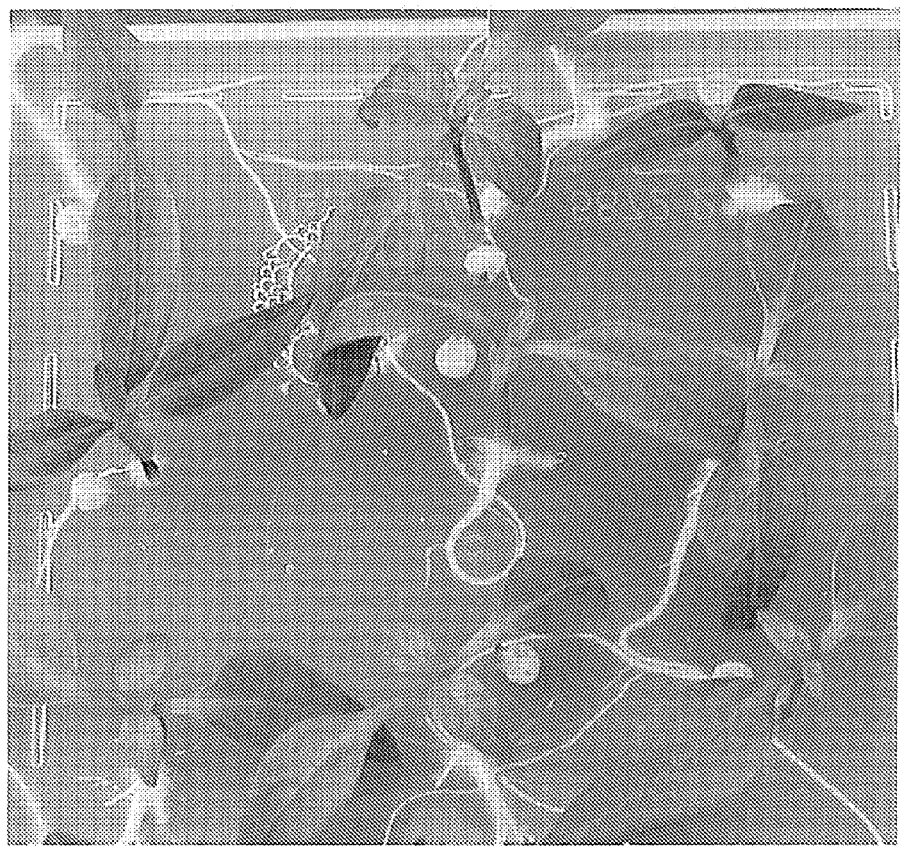
FIG. 10 shows segregating offspring on Km containing medium
Figure 11:
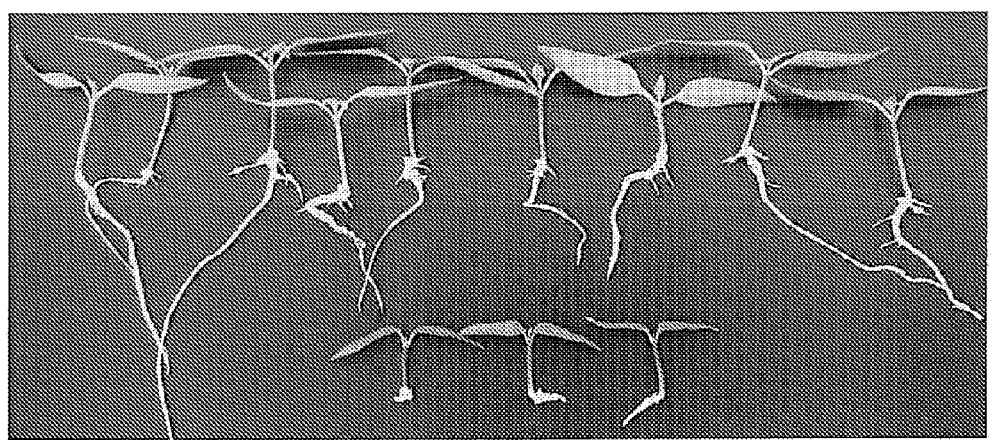
FIG. 11 shows the phenotypes of segregating transgenic plants. Upper row shows Km resistant seedlings, lower row shows Km susceptible seedlings

In total, more than 10000 explants of the three cultivars were co-cultivated with either the control or BBM construct. During the first 3 weeks of culture on selective medium all explants increased in size and small light green or whitish calli became visible. After an additional two weeks, callus formation and/or direct shoot formation occurred at the cut surface, depending on the type of cytokinin used. In the presence of TDZ, explants formed multiple shoot-like structures (SLS) while zeatin riboside induced predominantly callus and a reduced number of SLS (FIGS. 2 and 3). At this stage, explants transformed with 35S::BBM:GR produced more SLS than the control. After transfer to EM medium only 35S::BBM:GR SLS proliferated and formed either shoots or somatic embryos on the primary leaves within the following 3-4 weeks (FIGS. 4 and 5 and table 2). Germination, elongation and formation of proper shoots were all enhanced after transfer to PRM. Root formation occurred after transfer of elongated shoots to rooting medium within two weeks after transfer. Six months after transformation, rooted shoots were transferred to rock wool blocks and adapted to greenhouse conditions for seed production.

TABLE 2

|  | No explants | No SLS | % SLS | Rooted shoots |
| --- | --- | --- | --- | --- |
| 35S::BBM:GR | 5620 | 662 | 11.78 | 170 |
| 35S:BBM | 1128 | 11 | 0.98 | 0 |

Table 2 Shows a Comparison of Regeneration with Two BBM Constructs.

Figure 12:
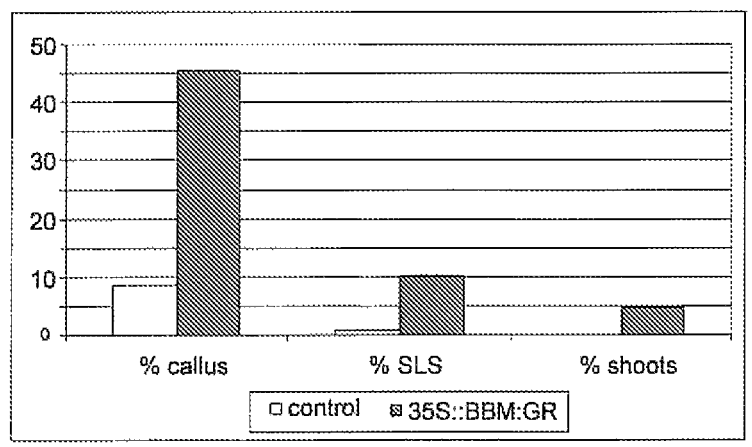
FIG. 12 shows percentage of callus, shoot-like structure (SLS), and shoot formation of cotyledonary explants transformed with either control or 35S::BBM:GR.

Transgenic shoots were produced from the transformations with 35S::BBM:GR construct but none from the control. Under the chosen conditions the control transformations showed callus production rather than shoot-like structures (SLS) or shoots (FIG. 12). From the three tested lines, Fiesta showed the highest regeneration capacity (48%), followed by Spirit (3,4%) and Ferrari (1,7%) (Table 3). After adaptation to greenhouse conditions, plants grew rapidly and flowered but stayed about 30% shorter than the non-transformed control plants. Selfings and crosses were performed successfully showing that fertility was not affected by the transformation and regeneration process.

The initiation of somatic embryogenesis resulted in multiple shoot formation of transgenic plants (FIG. 5). In total more than 20 independent transgenic plants from Fiesta and Ferrari deriving from several independent transformation experiments were generated. Molecular analysis by PCR on independent T0 plants derived from the same explant showed that all shoots are transgenic and that the overall transformation efficiency can vary between 0.5 and 1%, calculated from the initial number of explants used per transformation.

Segregation analysis showed that the transgene inherited according to the Mendelian pattern (Table 4).

TABLE 3

|  | Nr of explants | Nr of shoots | % |
| --- | --- | --- | --- |
| Ferrari | 886 | 15 | 1.7 |
| Fiesta | 1304 | 626 | 48 |
| Spirit | 1781 | 61 | 3.4 |

Table 3 shows the percentages of shoot formation of different varieties after transformation with 35S::BBM:GR.

TABLE 4

| plant ID | Background | n sown | Km R | Km S | ratio | n loci |
| --- | --- | --- | --- | --- | --- | --- |
| 1702 | Fiesta | 42 | 31 | 11 | 3:1 | 1 |
| 2559 | Fiesta | 100 | 74 | 24 | 3:1 | 1 |
| 2639 | Fiesta | 113 | 0 | 113 | 0:1 | 0 |
| 2647 | Fiesta | 78 | 0 | 78 | 0:1 | 0 |
| 2649 | Fiesta | 70 | 51 | 19 | 3:1 | 1 |
| 2650 | Fiesta | 50 | 32 | 14 | 3:1 | 1 |
| 2655 | Fiesta | 50 | 37 | 11 | 3:1 | 1 |
| 2656 | Fiesta | 63 | 48 | 15 | 3:1 | 1 |
| 2676 | Fiesta | 24 | 20 | 4 | 5:1 | >1 |
| 2691 | Fiesta | 14 | 13 | 1 | 13:1 | >1 |
| 2692 | Fiesta | 49 | 42 | 7 | 6:1 | >1 |
| 2693 | Fiesta | 100 | 98 | 2 | 49:1 | >1 |
| 2696 | Fiesta | 77 | 65 | 12 | 5:1 | >1 |
| 2697 | Fiesta | 100 | 75 | 25 | 3:1 | 1 |
| 2700 | Fiesta | 100 | 82 | 18 | 5:1 | >1 |
| 2831 | Ferrari | 79 | 69 | 10 | 7:1 | >1 |
| 2832 | Ferrari | 65 | 54 | 11 | 5:1 | >1 |
| 3041 | Ferrari | 100 | 75 | 25 | 3:1 | 1 |

Table 4 shows segregation analysis of offspring from self-fertilized mature transgenic plants grown on selective medium.

Discussion

The results show that by using an inducible overexpressed BBM gene, good quality shoots of transgenic sweet pepper plants can be regenerated directly or via somatic embryogenesis and that the transgene is inherited to the next generation.

The induction of somatic embryo formation in hot pepper species and varieties has been studied intensively leading to regeneration into normal plants. In sweet pepper, however, the induction of somatic embryos was possible but embryos lack the apical meristem and did not develop into normal plants. By activating the BBM-gene during the regeneration process it was possible to regenerate fertile sweet pepper plants.

Example 2

Genetic Transformation of Recalcitrant *Petunia* W138 with BBM

*Petunia* line W138 has been proven to be recalcitrant to regeneration and subsequent production of transgenic plants.

In an attempt to obtain mature transgenic *Petunia* plants, explants of W138 were transformed using a standard protocol for *petunia* transformation.

Two lines of W138 background (NC2676-10, NC2676-11) and one of W5 background (293) were transformed with the inducible BBM construct (35S::BBM::GR), or a control T-DNA construct, in this case containing the GUS reporter gene. Kanamycin resistant calli were obtained from all three lines with both constructs, with the highest efficiency for NC2676-11, followed by 293. Calli of the control construct showed strong GUS expression.

Shoot like structures (SLS) and primordia appeared first in line NC2676-11 followed by the others in the same order, however further development and outgrowth was observed only in calli transformed with 35S:BBM::GR (FIGS. 14 and 15).

Like in sweet pepper, overexpression of BBM leads to the formation of transgenic shoots in a recalcitrant plant.

Example 3

Progeny Analysis of 35S::BBM::GR Lines

Homozygous T1 progeny of multiple 35S::BBM::GR lines were grown in vitro on co-cultivation medium further comprising TDZ, DEX and/or TDZ and DEX or without TDZ/DEX as a control.

Cultivation of cotyledon explants from homozygous 35S::BBM:GR lines revealed developmental differences caused by the nuclear induced and non-nuclear induced BBM protein. At the rim of the cotyledon where it had been cut transversally, somatic embryos are formed (FIG. 19). These effects were not observed from cotyledon explants grown on medium without DEX.

Results herein show that controlled, exogenous BBM expression can be used to produce high quality, morphologically normal shoots of transgenic sweet pepper. Such somatic embryos indeed had a striking similarity to zygotic embryos. In fact, a high number (>100) of somatic embryos could be induced on pepper cotyledons. The high amount of such embryos that could be identified on pepper explants is sufficient to allow at least a 100-fold multiplication factor to be reached in the generation of mature sweet pepper plants in tissue culture. This finding also enables one to multiply male sterile sweet pepper plants without the need to use a maintainer line.

REFERENCES

Bent A F. (2000) *Arabidopsis* in planta transformation. Uses, mechanisms, and prospects for transformation of other species. Plant Physiol. 124:1540-7.

Broothaerts W, Mitchell H J, Weir B, Kaines S, Smith L M, Yang W, Mayer J E, Roa-Rodriguez C, Jefferson R A (2005) Gene transfer to plants by diverse species of bacteria. Nature 433:629-33.

De Witt and Bosland (1997) Pepper of the world: an identification guide. Ten Speed Press, Berkley.

Gamborg O. L. MRA, Ojima K. (1968) Nutrient Requirement of suspension cultures of soybean root cells. Experimental Cell Research 50

Murashige T, Skoog F (1962) A Revised Medium for Rapid Growth and Bio Assays with Tobacco Tissue Cultures. Physiologia Plantarum 15: 473-497.

---

The invention claimed is:

1. A method for providing a fertile transgenic plant comprising:
   a) transforming a recalcitrant sweet pepper *Capsicum annuum* or *Petunia hybrida* plant cell with an expression vector encoding a babyboom protein (BBM), wherein said expression vector provides inducible nuclear transcriptional activity of said babyboom protein (BBM), and wherein babyboom protein BBM is SEQ ID NO: 1 under the condition that said babyboom protein (BBM) has transcriptional activity;
   b) regenerating said recalcitrant transformed sweet pepper *Capsicum annuum* or *Petunia hybrida* plant cell into somatic embryos, shoot-like structures (SLS) and/or leaf-like structures (LLS) under inductive conditions resulting in nuclear transcriptional activity of said babyboom protein (BBM);
   c) culturing said somatic embryos, shoot-like structures (SLS) and/or leaf-like structures (LLS) into a fertile transgenic sweet pepper *Capsicum annuum* or *Petunia hybrida* plant under non-inductive conditions resulting in the substantial absence of nuclear transcriptional activity of said babyboom protein (BBM).

2. The method according to claim 1, wherein said inducible nuclear transcriptional activity is provided by a transcription regulation element, a nuclear targeting sequence, or a translation regulation element.

3. The method according to claim 2, wherein said nuclear targeting sequence is encoded by a nucleotide sequence according to SEQ ID NO: 2.

4. The method according to claim 3, wherein said inductive conditions are provided by dexamethasone.

5. The method according to claim 1, wherein said expression vector further encodes one or more selectable markers, one or more proteins of interest and/or one or more transcription products of interest.

6. The method according to claim 1, wherein said method further comprises:
   d) obtaining a plant cell from said fertile transgenic sweet pepper *Capsicum annuum* or *Petunia hybrida* plant;
   e) transforming said sweet pepper *Capsicum annuum* or *Petunia hybrida* plant cell with an expression vector encoding one or more proteins or transcription products of interest;
   f) regenerating said transformed sweet pepper *Capsicum annuum* or *Petunia hybrida* plant cell into somatic embryos, shoot-like structures (SLS) and/or leaf-like structures (LLS) under inductive conditions resulting in nuclear transcriptional activity of said babyboom protein (BBM);
   g) culturing said somatic embryos, shoot-like structures (SLS) and/or leaf-like structures into a fertile transgenic sweet pepper *Capsicum annuum* or *Petunia hybrida* plant under non-inductive conditions resulting in the absence of nuclear transcriptional activity of said babyboom protein (BBM);
   h) optionally repeating steps (d) to (g) one or more times.

7. A fertile transgenic sweet pepper *Capsicum annuum* or *Petunia hybrida* plant comprising one or more expression vectors that encode a babyboom protein (BBM) having the sequence of SEQ ID NO: 1, wherein said expression vector provides inducible nuclear transcriptional activity of said babyboom protein (BBM).

8. A seed from the fertile plant according to claim 7 that comprises the expression vector of claim 7.

9. The method according to claim 1, wherein said plant cell is a *Petunia hybrida* plant cell.

10. The fertile transgenic plant according to claim 7, wherein said plant is a *Petunia hybrida*.

11. The fertile transgenic plant according to claim 7, wherein said plant is a sweet pepper *Capsicum annum*.

12. A fruit from the fertile plant according to claim 7 that comprises the expression vector of claim 7.

13. The method according to claim 1, wherein said plant cell is a *Capsicum annum* plant cell.

14. The fertile transgenic sweet pepper *Capsicum annuum* or *Petunia hybrida* plant according to claim 7, wherein said plant is a sweet pepper *Capsicum annuum* deposited under number NCIMB 41732.

15. A plant part from the fertile plant according to claim 7 that comprises the expression vector of claim 7.

* * * * *

UNITED STATES PATENT AND TRADEMARK OFFICE
CERTIFICATE OF CORRECTION

PATENT NO. : 9,212,369 B2  
APPLICATION NO. : 13/383312  
DATED : December 15, 2015  
INVENTOR(S) : Iris Heidmann et al.

It is certified that error appears in the above-identified patent and that said Letters Patent is hereby corrected as shown below:

On the Title Page of the Patent, Column 2, OTHER PUBLICATIONS, Line 25, delete "emryogenesis" and insert -- embryogenesis --

On the Title Page of the Patent, Column 2, OTHER PUBLICATIONS, Line 26, delete "Botony," and insert -- Botany, --

IN THE CLAIMS

Column 23, Line 39, Claim 1, delete "BBM" and insert -- (BBM) --

Column 24, Line 46, Claim 6, delete "structures" and insert -- structures (LLS) --

Signed and Sealed this  
Twenty-sixth Day of April, 2016

Michelle K. Lee  
*Director of the United States Patent and Trademark Office*

SEQUENCE LISTING

```
<160> NUMBER OF SEQ ID NOS: 3

<210> SEQ ID NO 1
<211> LENGTH: 579
<212> TYPE: PRT
<213> ORGANISM: Brassica napus

<400> SEQUENCE: 1

Met Asn Asn Asn Trp Leu Gly Phe Ser Leu Ser Pro Tyr Glu Gln Asn
1               5                   10                  15

His His Arg Lys Asp Val Tyr Ser Ser Thr Thr Thr Val Val Asp
            20                  25                  30

Val Ala Gly Glu Tyr Cys Tyr Asp Pro Thr Ala Ala Ser Asp Glu Ser
        35                  40                  45

Ser Ala Ile Gln Thr Ser Phe Pro Ser Pro Phe Gly Val Val Val Asp
    50                  55                  60

Ala Phe Thr Arg Asp Asn Asn Ser His Ser Arg Asp Trp Asp Ile Asn
65                  70                  75                  80

Gly Cys Ala Cys Asn Asn Ile His Asn Asp Glu Gln Asp Gly Pro Lys
                85                  90                  95

Leu Glu Asn Phe Leu Gly Arg Thr Thr Thr Ile Tyr Asn Thr Asn Glu
            100                 105                 110

Asn Val Gly Asp Gly Ser Gly Ser Gly Cys Tyr Gly Gly Gly Asp Gly
        115                 120                 125

Gly Gly Gly Ser Leu Gly Leu Ser Met Ile Lys Thr Trp Leu Arg Asn
```

-continued

```
               130                 135                 140
Gln Pro Val Asp Asn Val Asp Asn Gln Glu Asn Gly Asn Ala Ala Lys
145                 150                 155                 160

Gly Leu Ser Leu Ser Met Asn Ser Ser Thr Ser Cys Asp Asn Asn Asn
                165                 170                 175

Asp Ser Asn Asn Asn Val Val Ala Gln Gly Lys Thr Ile Asp Asp Ser
                180                 185                 190

Val Glu Ala Thr Pro Lys Lys Thr Ile Glu Ser Phe Gly Gln Arg Thr
                195                 200                 205

Ser Ile Tyr Arg Gly Val Thr Arg His Arg Trp Thr Gly Arg Tyr Glu
                210                 215                 220

Ala His Leu Trp Asp Asn Ser Cys Lys Arg Glu Gly Gln Thr Arg Lys
225                 230                 235                 240

Gly Arg Gln Val Tyr Leu Gly Gly Tyr Asp Lys Glu Lys Ala Ala
                245                 250                 255

Arg Ala Tyr Asp Leu Ala Ala Leu Lys Tyr Trp Gly Thr Thr Thr Thr
                260                 265                 270

Thr Asn Phe Pro Met Ser Glu Tyr Glu Lys Glu Val Glu Glu Met Lys
                275                 280                 285

His Met Thr Arg Gln Glu Tyr Val Ala Ser Leu Arg Arg Lys Ser Ser
                290                 295                 300

Gly Phe Ser Arg Gly Ala Ser Ile Tyr Arg Gly Val Thr Arg His His
305                 310                 315                 320

Gln His Gly Arg Trp Gln Ala Arg Ile Gly Arg Val Ala Gly Asn Lys
                325                 330                 335

Asp Leu Tyr Leu Gly Thr Phe Gly Thr Gln Glu Glu Ala Ala Glu Ala
                340                 345                 350

Tyr Asp Ile Ala Ala Ile Lys Phe Arg Gly Leu Thr Ala Val Thr Asn
                355                 360                 365

Phe Asp Met Asn Arg Tyr Asn Val Lys Ala Ile Leu Glu Ser Pro Ser
                370                 375                 380

Leu Pro Ile Gly Ser Ala Ala Lys Arg Leu Lys Glu Ala Asn Arg Pro
385                 390                 395                 400

Val Pro Ser Met Met Met Ile Ser Asn Asn Val Ser Glu Ser Glu Asn
                405                 410                 415

Ser Ala Ser Gly Trp Gln Asn Ala Ala Val Gln His Gln Gly Val
                420                 425                 430

Asp Leu Ser Leu Leu His Gln His Gln Glu Arg Tyr Asn Gly Tyr Tyr
                435                 440                 445

Tyr Asn Gly Gly Asn Leu Ser Ser Glu Ser Ala Arg Ala Cys Phe Lys
                450                 455                 460

Gln Glu Asp Asp Gln His His Phe Leu Ser Asn Thr Gln Ser Leu Met
465                 470                 475                 480

Thr Asn Ile Asp His Gln Ser Ser Val Ser Asp Asp Ser Val Thr Val
                485                 490                 495

Cys Gly Asn Val Val Gly Tyr Gly Gly Tyr Gln Gly Phe Ala Ala Pro
                500                 505                 510

Val Asn Cys Asp Ala Tyr Ala Ala Ser Glu Phe Asp Tyr Asn Ala Arg
                515                 520                 525

Asn His Tyr Tyr Phe Ala Gln Gln Gln Gln Thr Gln Gln Ser Pro Gly
                530                 535                 540

Gly Asp Phe Pro Ala Ala Met Thr Asn Asn Val Gly Ser Asn Met Tyr
545                 550                 555                 560
```

Tyr His Gly Glu Gly Gly Gly Glu Val Ala Pro Thr Phe Thr Val Trp
            565                 570                 575

Asn Asp Asn

<210> SEQ ID NO 2
<211> LENGTH: 861
<212> TYPE: DNA
<213> ORGANISM: Artificial Sequence
<220> FEATURE:
<223> OTHER INFORMATION: Dexamethasone induction system

<400> SEQUENCE: 2

```
tctacaaaga aaaaaatcaa agggattcag caagccactg caggagtctc acaagacact      60
tcggaaaatc ctaacaaaac aatagttcct gctgcattac acagctcac ccctaccttg      120
gtgtcactgc tggaggtgat tgaacccgag gtgttgtatg caggatatga tagctctgtt     180
ccagattcag cgtggagaat tatgaccaca ctcaacatgt taggtgggcg tcaagtgatt     240
gcagcagtga atgggcaaa ggcgatacca ggcttcagaa acttacacct ggatgaccaa      300
atgaccctgc tacagtactc atggatgttt ctcatggcat ttgccctggg ttggagatca     360
tacagacaat caagtggaaa cctgctctgc tttgctcctg atctgattat taatgagcag     420
agaatgtctc taccctgcat gtatgaccaa tgtaaacaca tgctgtttgt ctcctctgaa     480
ttacaaagat tgcaggtatc ctatgaagag tatctctgta tgaaaacctt actgcttctc     540
tcctcagttc ctaaggaagg tctgaagagc caagagttat ttgatgagat tcgaatgact    600
tatatcaaag agctaggaaa agccatcgtc aaaaggggag ggaactccag tcagaactgg   660
caacggtttt accaactgac aaagcttctg gactccatgc atgaggtggt tgagaatctc    720
cttacctact gcttccagac attttttggat aagaccatga gtattgagtt cccagagatg   780
ttagctgaaa tcatcactaa tcagatacca aaatattcaa atggaaatat caaaaagctc    840
ctgtttcatc aaaaatgact g                                               861
```

<210> SEQ ID NO 3
<211> LENGTH: 1740
<212> TYPE: DNA
<213> ORGANISM: Brassica napus

<400> SEQUENCE: 3

```
atgaataata actggttagg ctttctctc tctccttatg aacaaaatca ccatcgtaag      60
gacgtctact cttccaccac cacaaccgtc gtagatgtcg ccggagagta ctgttacgat     120
ccgaccgctg cctccgatga gtcttcagcc atccaaacat cgtttccttc tcccttgt      180
gtcgtcgtcg atgctttcac cagagacaac aatagtcact cccgagattg gacatcaat     240
ggttgtgcat gcaataacat ccacaacgat gagcaagatg gaccaaagct tgagaatttc    300
cttggccgca ccaccacgat ttacaacacc aacgaaaacg ttggagatgg aagtggaagt    360
ggctgttatg gaggaggaga cggtggtggt ggctcactag gactttcgat gataaagaca    420
tggctgagaa atcaacccgt ggataatgtt gataatcaag aaaatggcaa tgctgcaaaa    480
ggcctgtccc tctcaatgaa ctcatctact tcttgtgata caacaacga cagcaataac    540
aacgttgttg cccaagggaa gactattgat gatagcgttg aagctacacc gaagaaaact    600
attgagagtt ttggacagag gacgtctata taccgcggtg ttacaaggca tcggtggaca    660
ggaagatatg aggcacattt atgggataat agttgtaaaa gagaaggcca aacgcgcaaa    720
ggaagacaag ttatttggg aggttatgac aaagaagaaa aagcagctag gcttatgat     780
```

```
ttagccgcac tcaagtattg gggaaccacc actactacta acttccccat gagcgaatat    840
gaaaaagagg tagaagagat gaagcacatg acaaggcaag agtatgttgc ctcactgcgc    900
aggaaaagta gtggtttctc tcgtggtgca tcgatttatc gtggagtaac aagacatcac    960
caacatggaa gatggcaagc taggatagga agagtcgccg gtaacaaaga cctctacttg   1020
ggaacttttg gcacacaaga agaagctgca gaggcatacg acattgcggc catcaaattc   1080
agaggattaa ccgcagtgac taacttcgac atgaacagat acaacgttaa agcaatcctc   1140
gaaagcccta gtcttcctat tggtagcgcc gcaaaacgtc tcaaggaggc taaccgtccg   1200
gttccaagta tgatgatgat cagtaataac gtttcagaga gtgagaatag tgctagcggt   1260
tggcaaaacg ctgcggttca gcatcatcag ggagtagatt tgagcttatt gcaccaacat   1320
caagagaggt acaatggtta ttattacaat ggaggaaact tgtcttcgga gagtgctagg   1380
gcttgtttca aacaagagga tgatcaacac catttcttga gcaacacgca gagcctcatg   1440
actaatatcg atcatcaaag ttctgtttcg gatgattcgg ttactgtttg tggaaatgtt   1500
gttggttatg gtggttatca aggatttgca gccccggtta actgcgatgc ctacgctgct   1560
agtgagtttg attataacgc aagaaaccat tattactttg ctcagcagca gcagacccag   1620
cagtcgccag gtggagattt tcccgcggca atgacgaata atgttggctc taatatgtat   1680
taccatgggg aaggtggtgg agaagttgct ccaacattta cagtttggaa cgacaattag   1740
```